United States Patent
Wang et al.

(10) Patent No.: US 12,048,752 B2
(45) Date of Patent: Jul. 30, 2024

(54) LIPID MICROBUBBLES AND PROCESS OF MAKING THEREOF

(71) Applicant: TRUST BIOSONICS INC., Hsinchu County (TW)

(72) Inventors: ChungHsin Wang, Taipei (TW); ChienYu Ting, Taichung (TW)

(73) Assignee: Trust BioSonics Inc., Hsinchu County (TW)

( * ) Notice: Subject to any disclaimer, the term of this patent is extended or adjusted under 35 U.S.C. 154(b) by 0 days.

(21) Appl. No.: 17/830,165

(22) Filed: Jun. 1, 2022

(65) Prior Publication Data

US 2022/0296733 A1  Sep. 22, 2022

Related U.S. Application Data

(63) Continuation of application No. 16/073,566, filed as application No. PCT/US2017/016094 on Feb. 1, 2017, now abandoned.

(60) Provisional application No. 62/289,588, filed on Feb. 1, 2016.

(51) Int. Cl.
  *A61K 49/22* (2006.01)
  *A61K 47/02* (2006.01)
  *A61K 47/14* (2017.01)
  *A61K 47/24* (2006.01)

(52) U.S. Cl.
  CPC .......... *A61K 49/223* (2013.01); *A61K 49/226* (2013.01); *A61K 47/02* (2013.01); *A61K 47/14* (2013.01); *A61K 47/24* (2013.01); *A61K 2123/00* (2013.01)

(58) Field of Classification Search
  CPC .............. A61K 49/226; A61K 2123/00; A61K 47/24; A61K 47/14; A61K 47/02; A61K 49/223
  See application file for complete search history.

(56) References Cited

U.S. PATENT DOCUMENTS

2008/0152594 A1* 6/2008 Bussat .................... A61P 35/00
                                                      424/9.5
2014/0328767 A1* 11/2014 Wang ................... A61K 49/223
                                                      261/130

OTHER PUBLICATIONS

Abdalkader et al., Acta Biomaterials, 2015, 19, p. 112-118. (Year: 2016).*
Lozano et al., Langmuir, 2009, 25, p. 3705-3712. (Year: 2009).*

* cited by examiner

*Primary Examiner* — Michael G. Hartley
*Assistant Examiner* — Leah H Schlientz

(57) ABSTRACT

Disclosed is a suspension of gas-filled microbubbles in a physiologically acceptable liquid carrier comprising a lipid mixture of a first lipid having transition temperature of about 41° C. such as DPPC or DPPG, a second lipid having transition temperature of about 55° C. such as DSPC or DSPG, and a PEGylated DSPE such as DSPE-PEG2000, DSPE-PEG3000, or DSPE-PEG5000, and methods of preparation thereof.

12 Claims, 16 Drawing Sheets

FIG. 1A-B
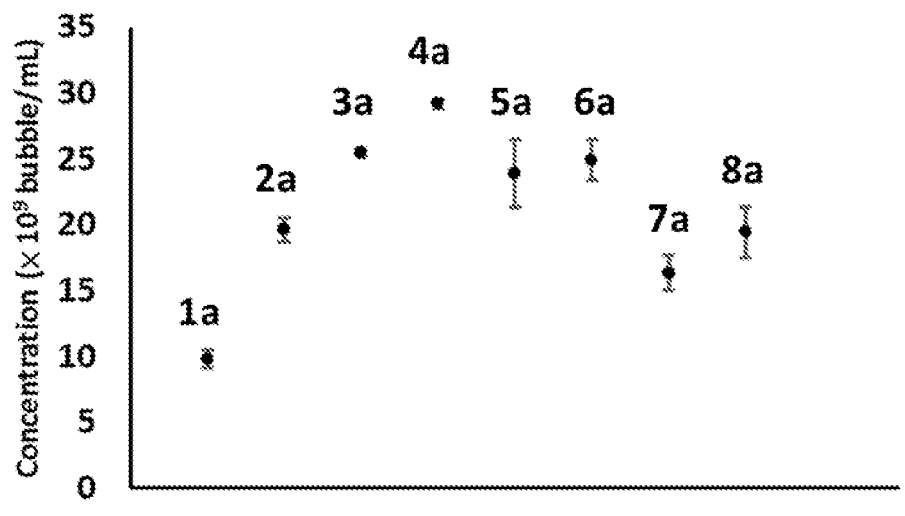
1A
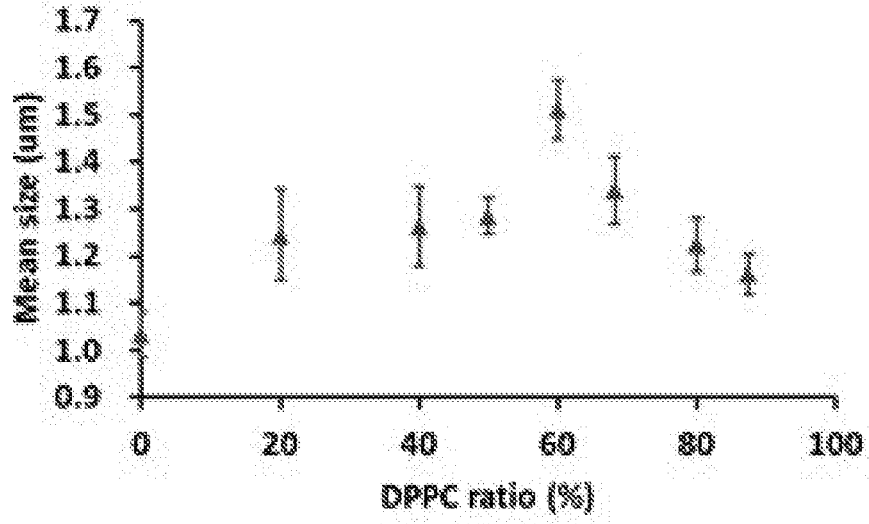
1B

FIG. 2A-B
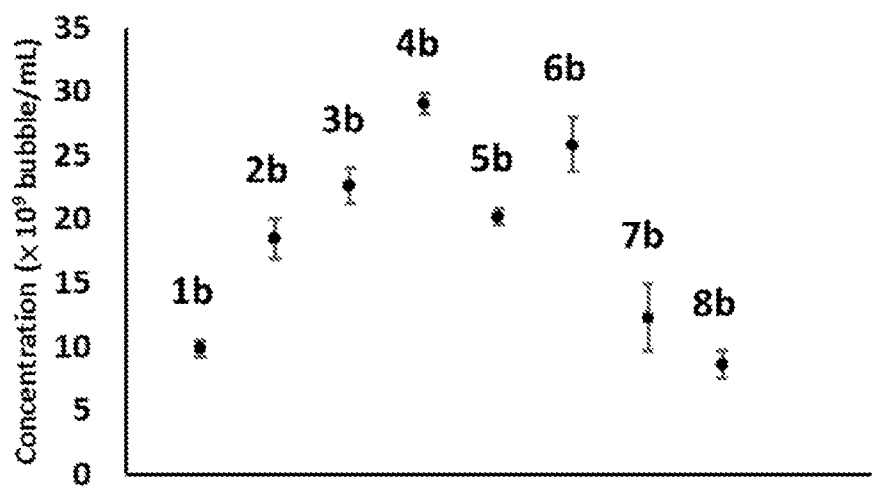
2A
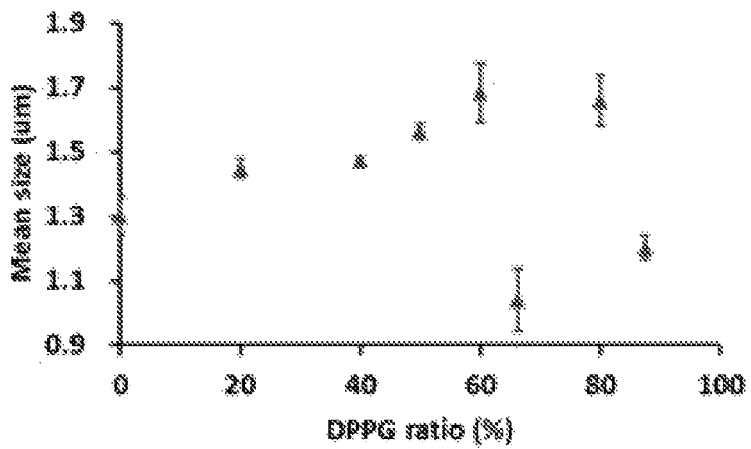
2B

FIG. 4A-B
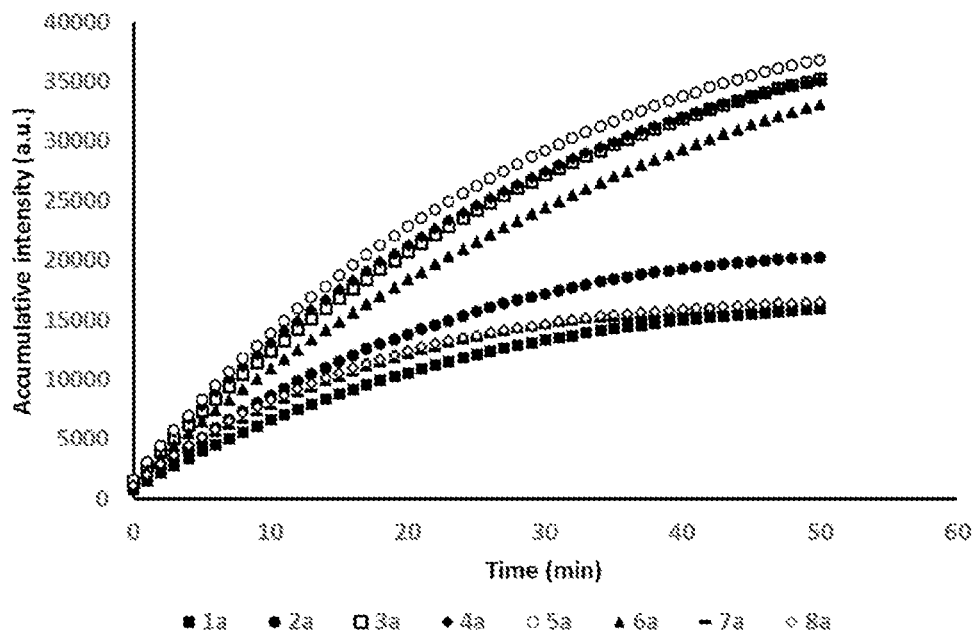
4A
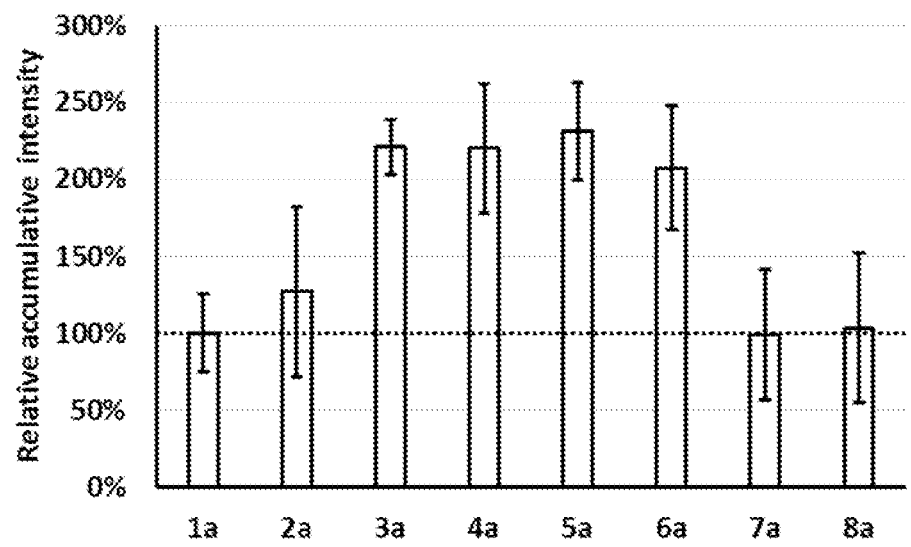
4B

FIG. 6A-B
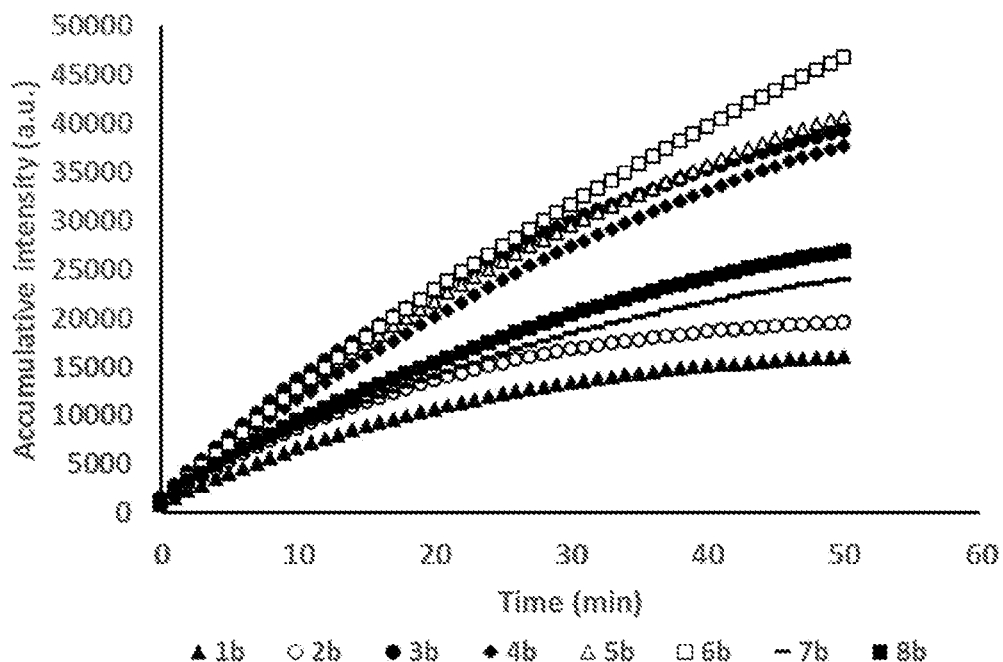
6A
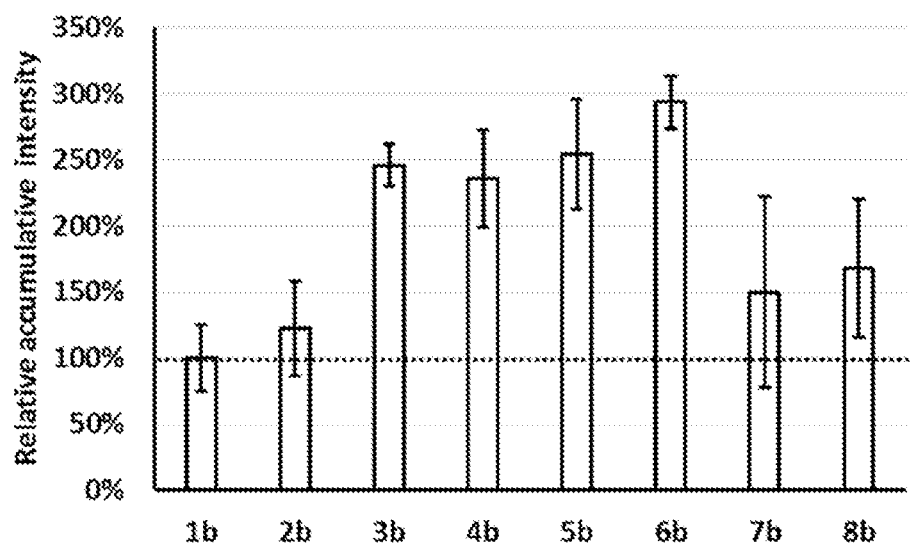
6B

FIG. 7A-B
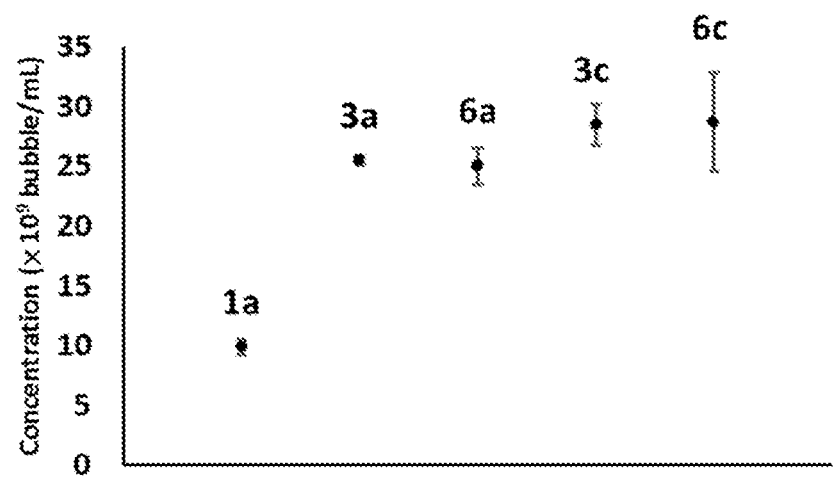
7A
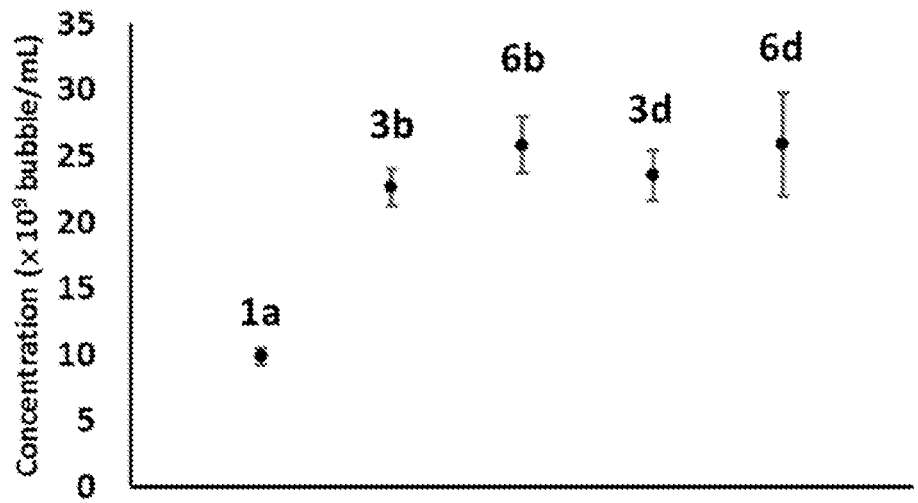
7B

FIG. 8A-B
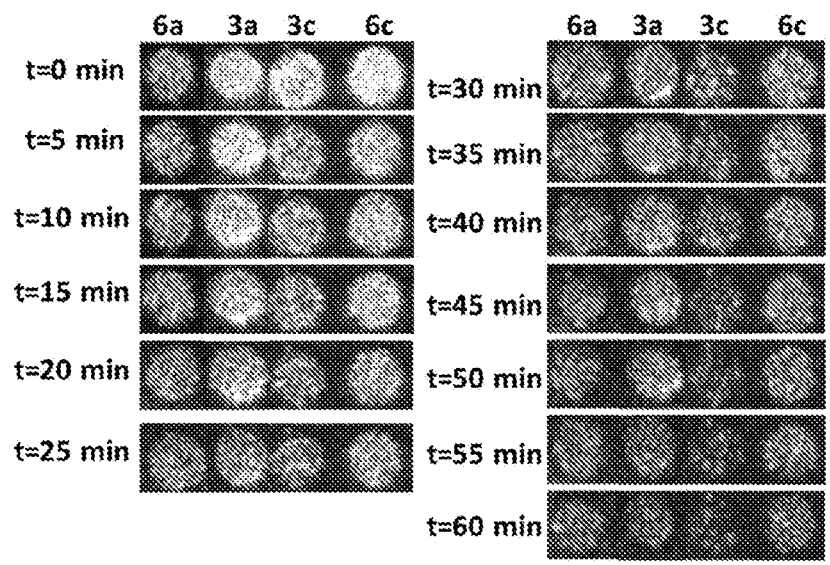
8A
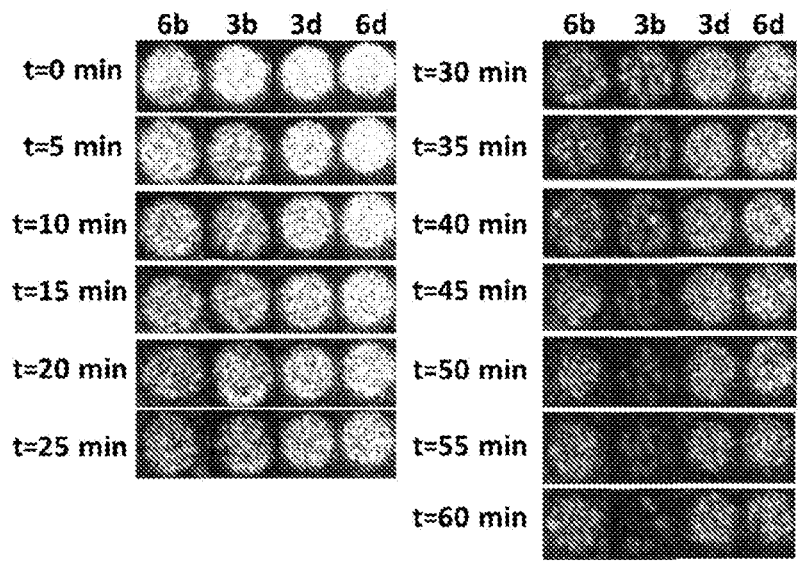
8B

FIG. 8C-D
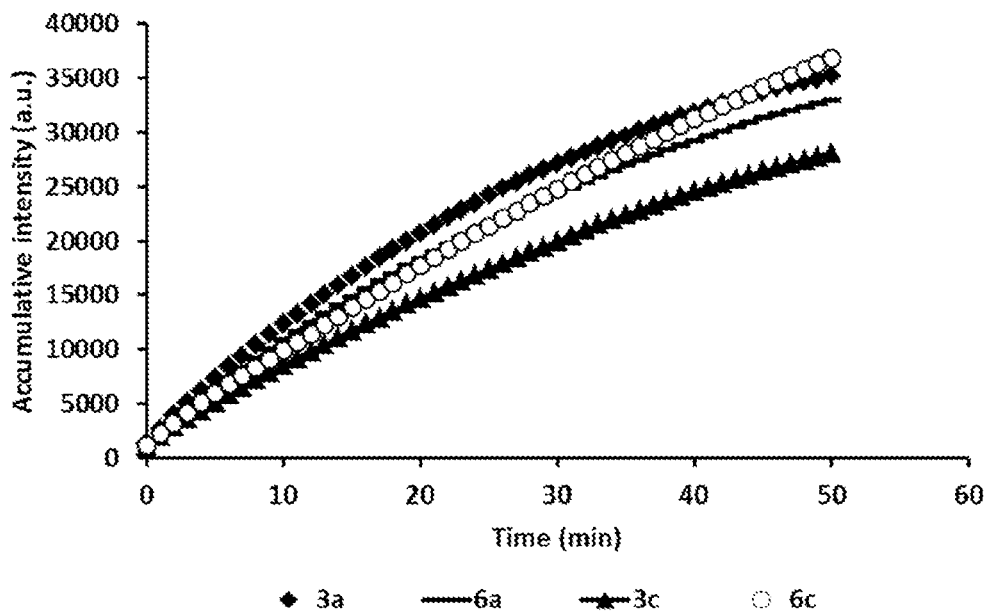
8C
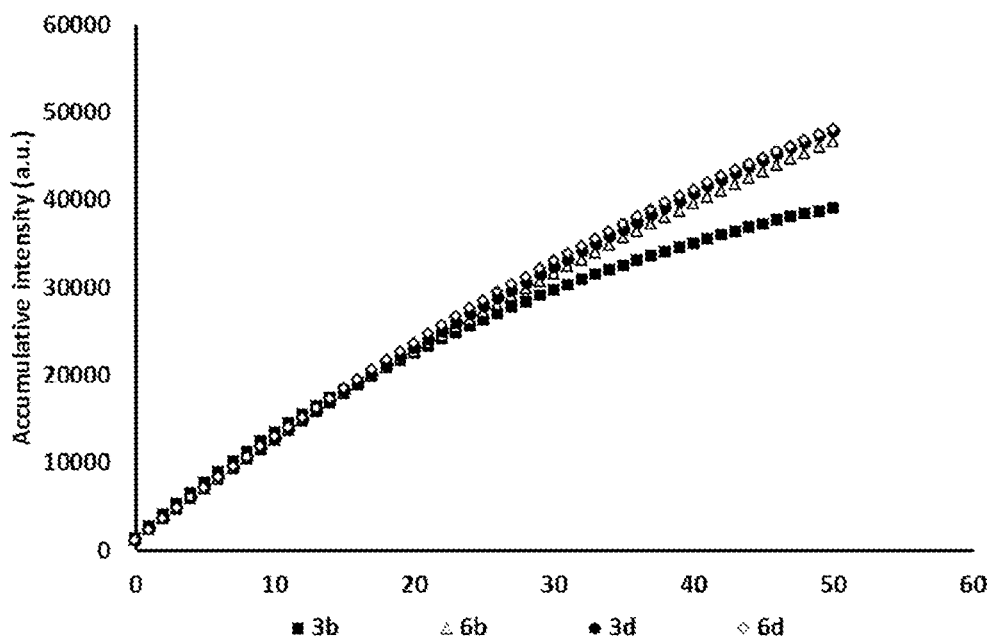
8D

FIG. 8E-F
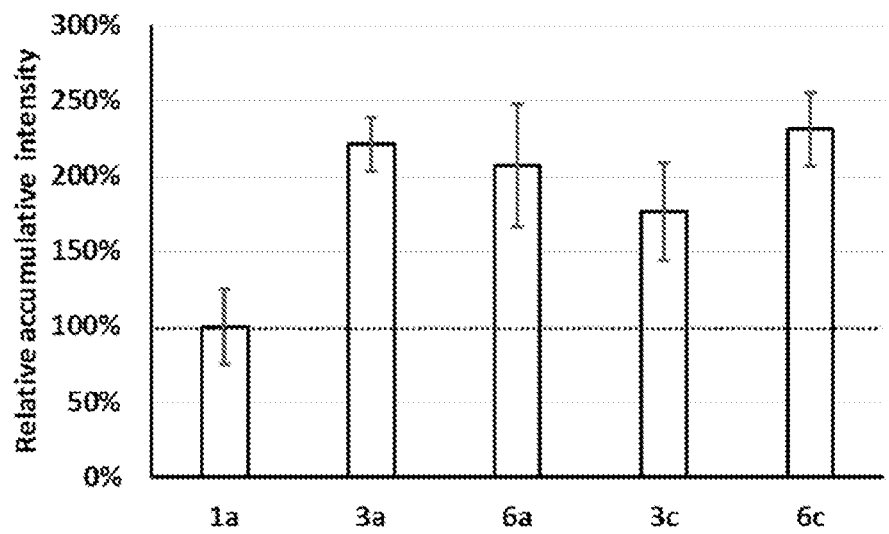
8E
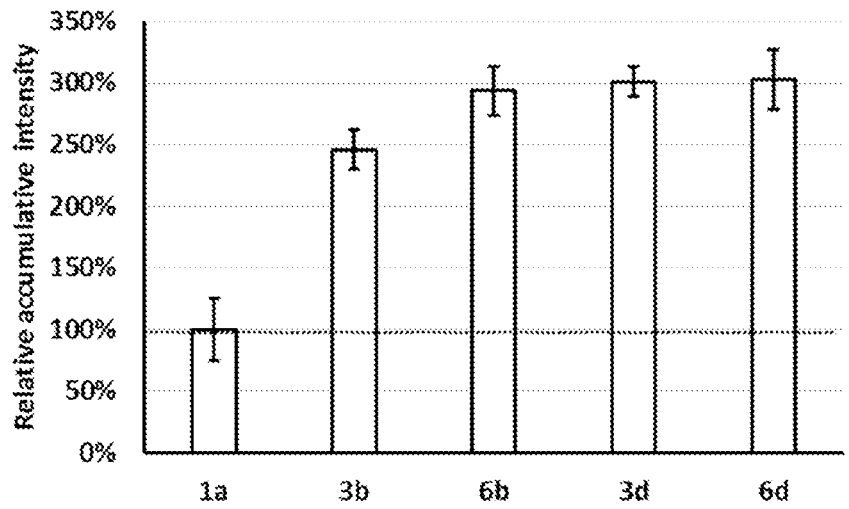
8F

FIG. 9A-B
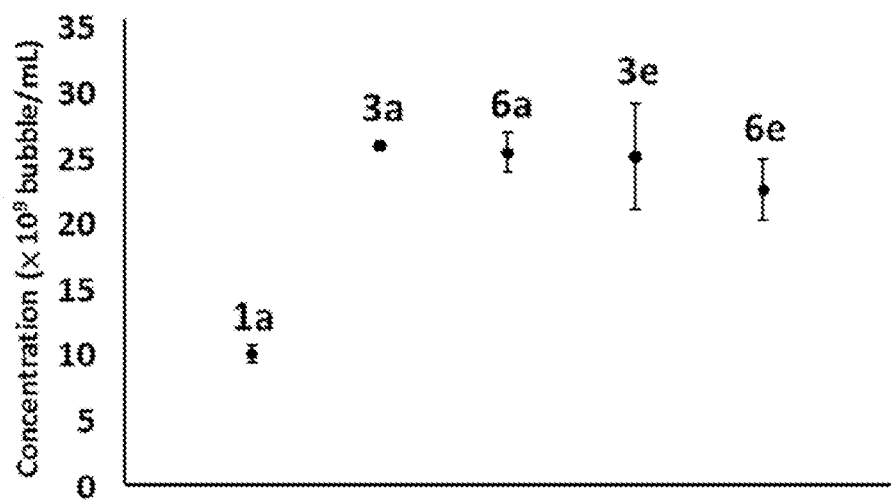
9A
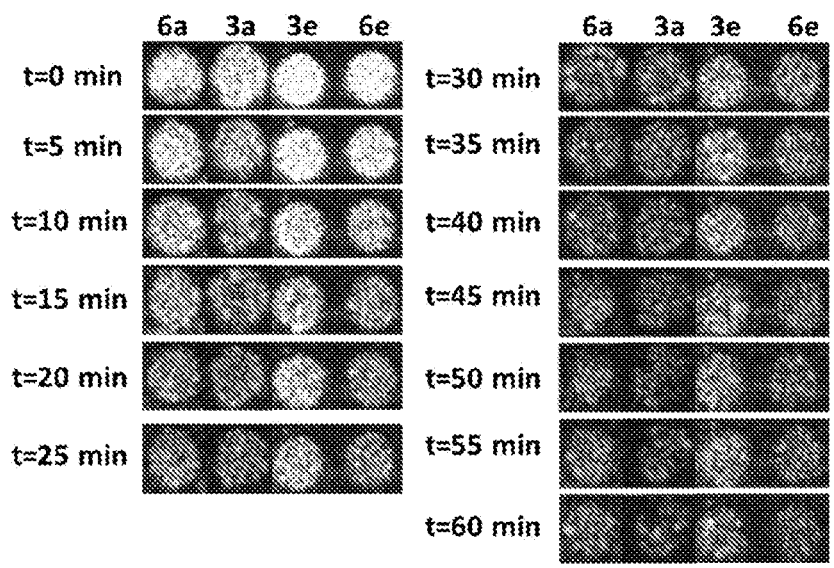
9B

FIG. 9C-D
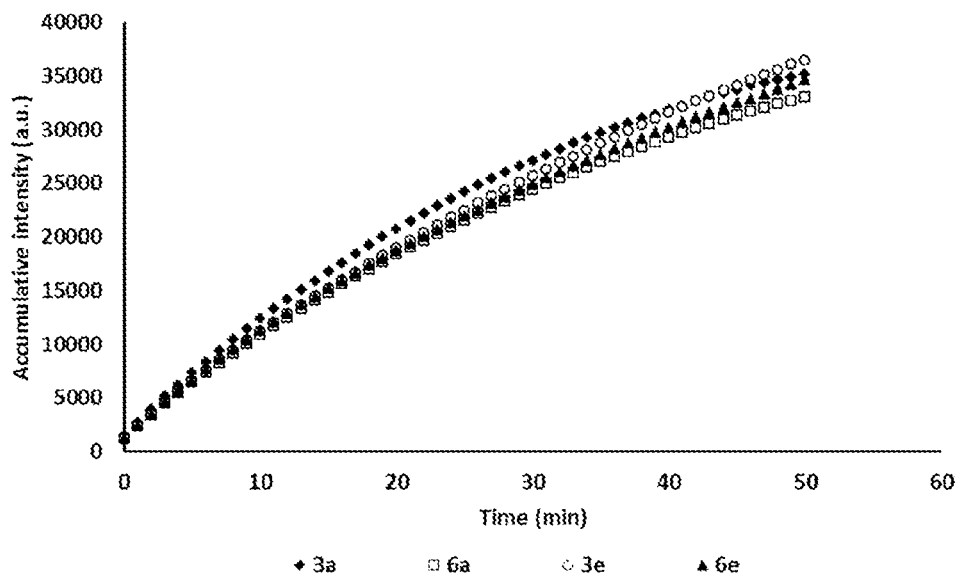
9C
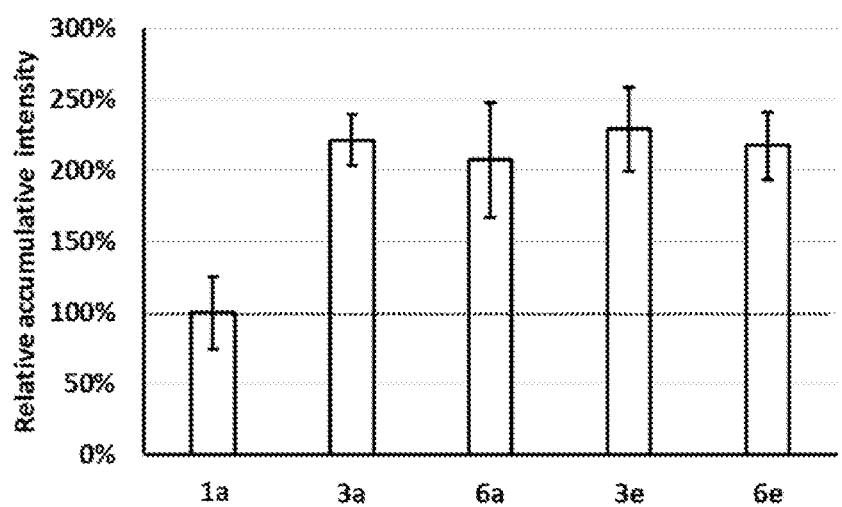
9D

FIG. 10A-B
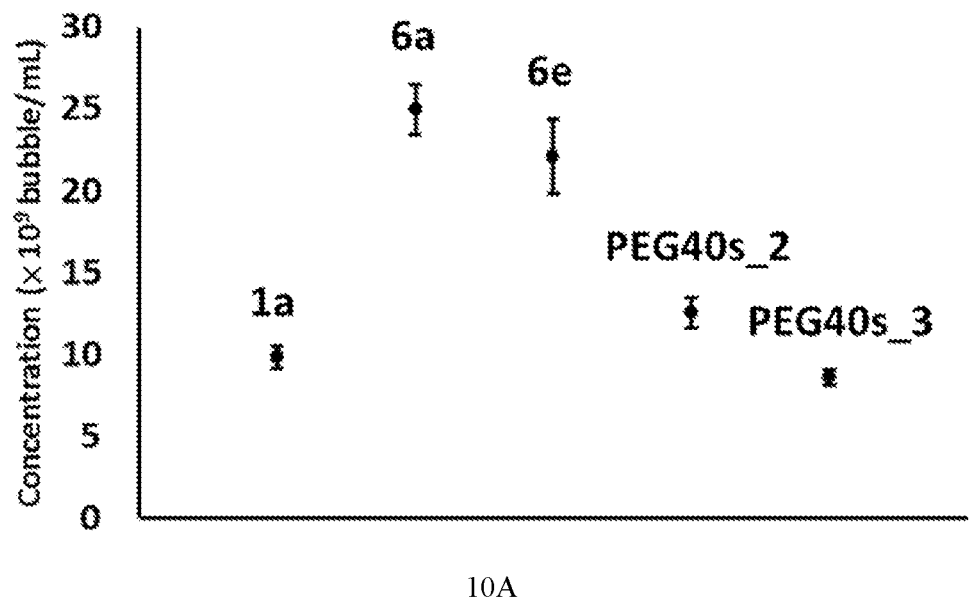
10A
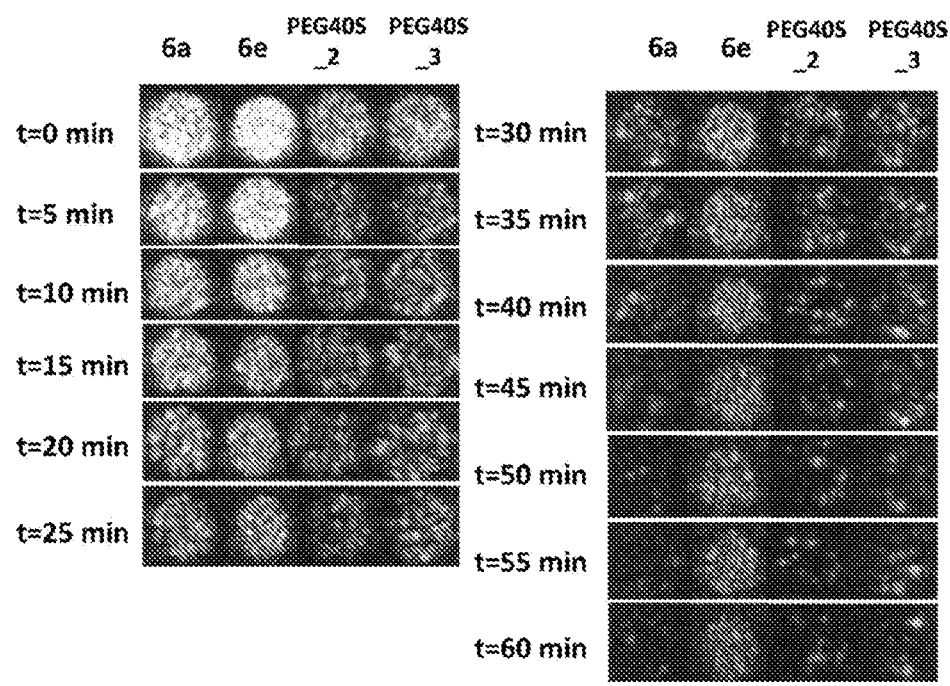
10B

FIG. 10C-D
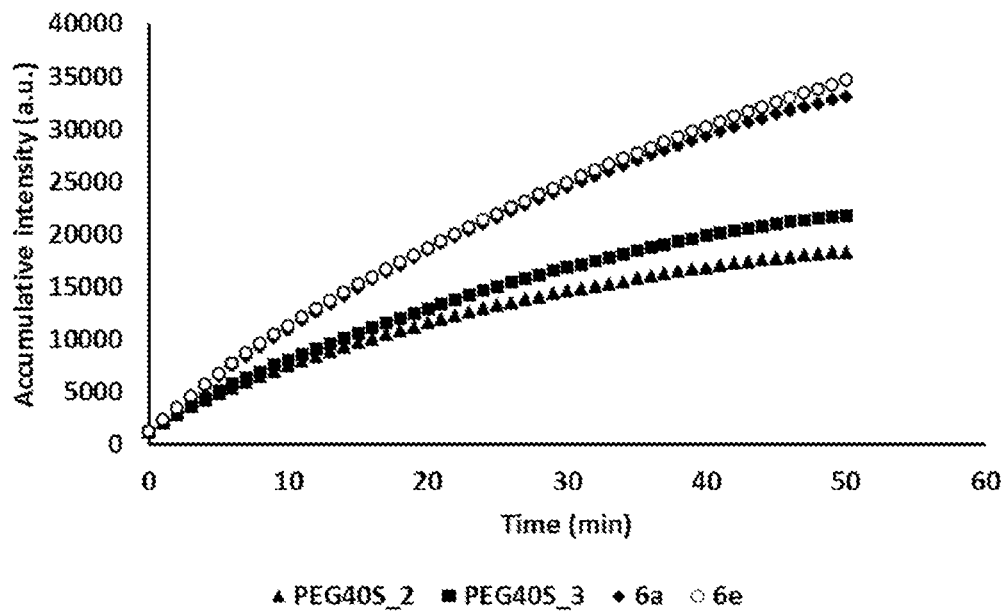
10C
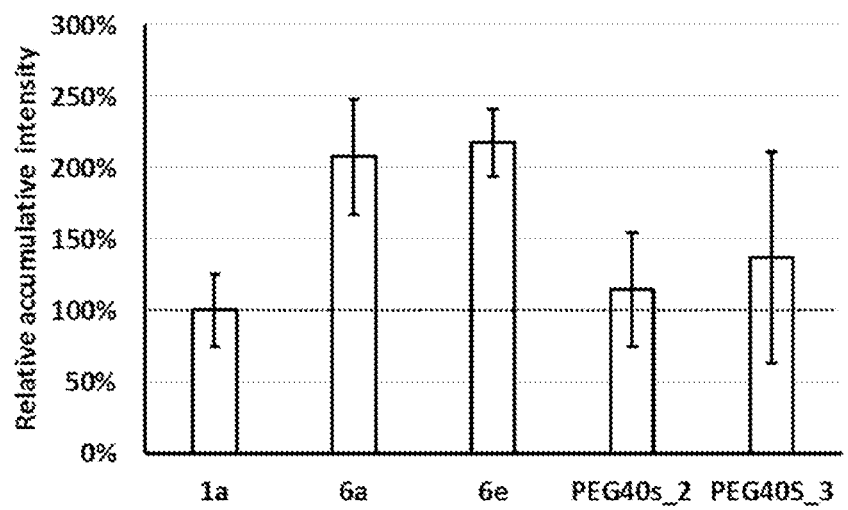
10D

11A-B
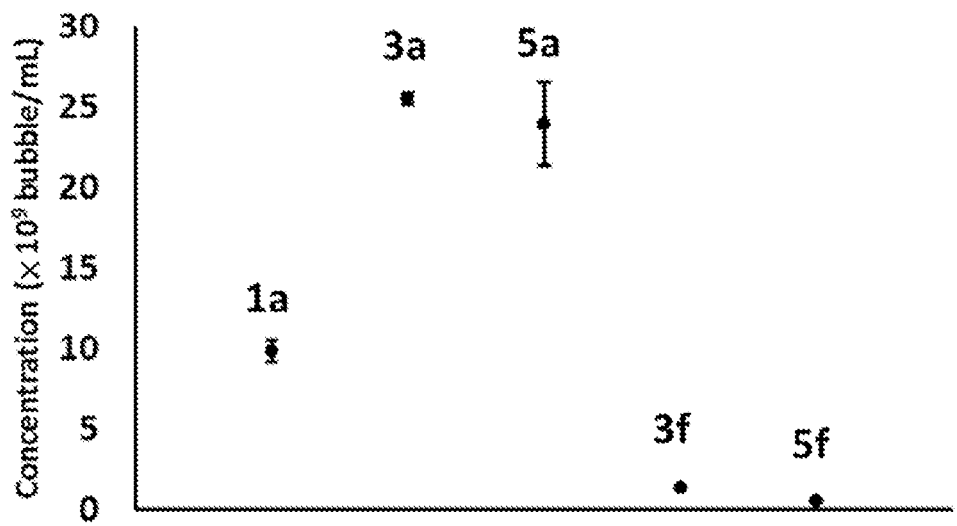
11A
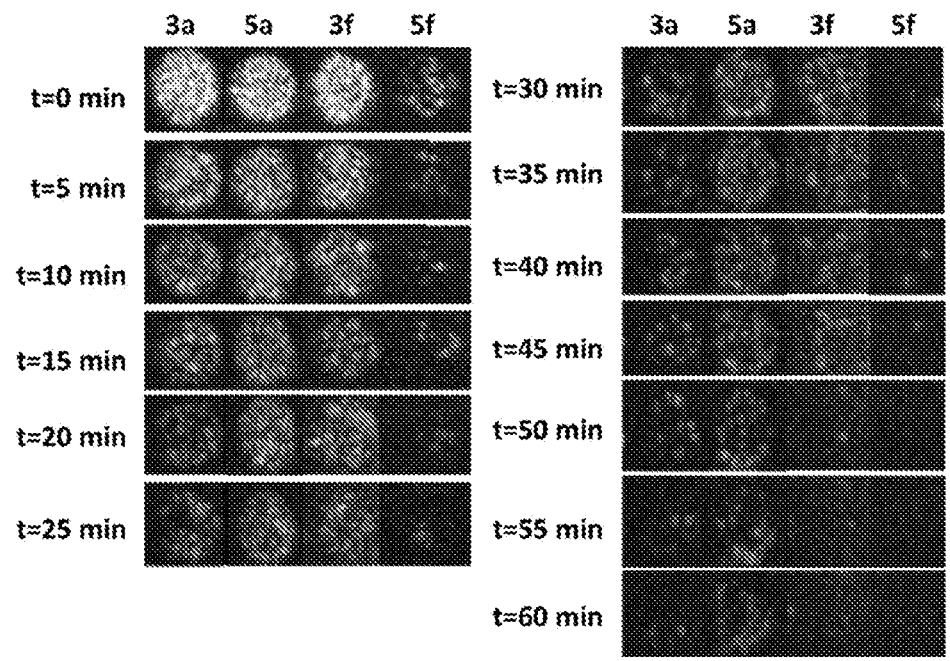
11B

11C-D
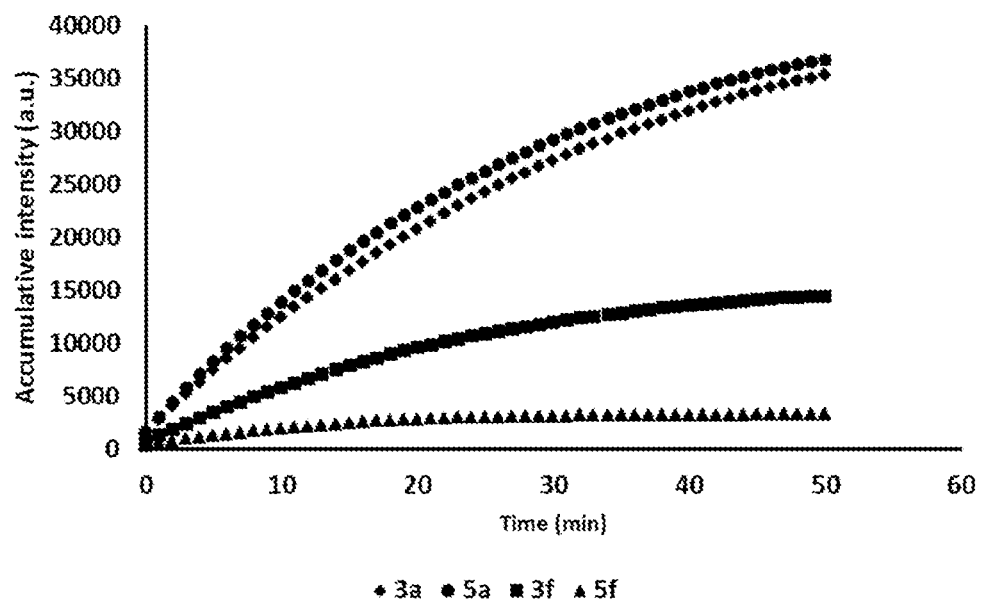
11C
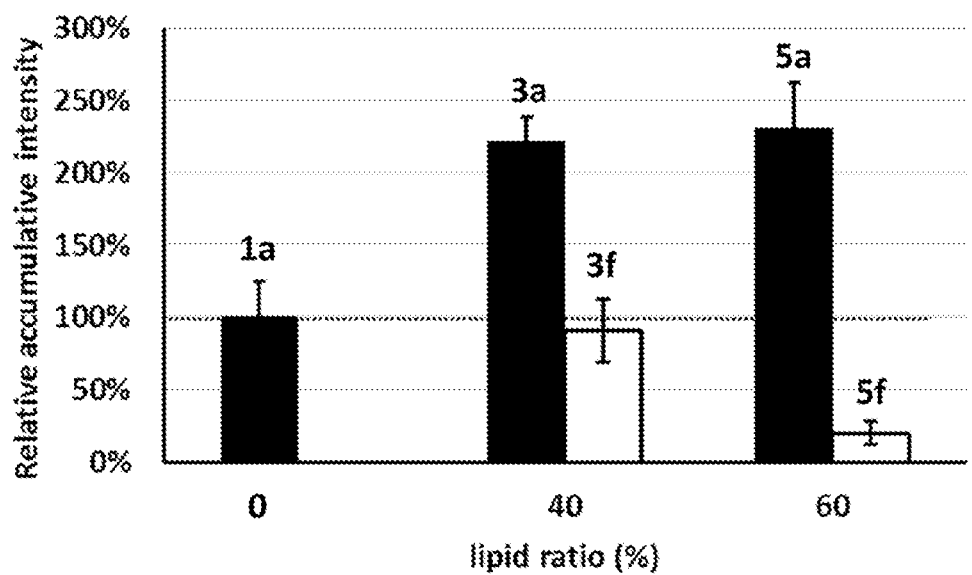
11D

LIPID MICROBUBBLES AND PROCESS OF MAKING THEREOF

BACKGROUND OF THE INVENTION

Contrast-enhanced ultrasound is the application of ultrasound contrast medium to traditional medical sonography. Commercially available contrast media are gas-filled microbubbles that are administered intravenously to the systemic circulation. There are a variety of microbubbles contrast agents. Microbubbles differ in their shell makeup, gas core makeup, and whether or not they are targeted. Regardless of the shell or gas core composition, microbubble size is fairly uniform. They lie within a range of 1-5 micrometers in diameter. Such micro-bubble-based ultrasound contrast agent can circulate well in the blood stream and provide a significant echo-enhancement of perfusion in ultrasound imaging.

SUMMARY OF THE INVENTION

In accordance with the present invention, the present invention provides a suspension of gas-filled microbubbles in a physiologically acceptable liquid carrier, said microbubbles comprising (a) a lipid mixture comprising a first lipid having transition temperature of about 41° C., a second lipid having transition temperature of about 55° C., and a PEGylated DSPE, and (b) a biocompatible gas, wherein the ratio of said first lipid is in a range of 40% to 63% by weight in the lipid mixture.

In one aspect, provided herein is a seal vial comprising (a) a lipid mixture comprising a first lipid having transition temperature of about 41° C., a second lipid having transition temperature of about 55° C., and a PEGylated DSPE, and (b) a biocompatible gas, and wherein the ratio of said first lipid is in a range of 40% to 63% by weight in the lipid mixture.

In another aspect provides methods of preparing the suspensions of gas-filled microbubbles or the seal vials disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-B show concentrations (1A) and mean size (1B) of the formed microbubbles from sample numbers 1a-8a in various DPPC ratio.

FIGS. 2A-B show concentrations (2A) and mean size (2B) of the formed microbubbles from sample numbers 1b-8b in various DPPG ratio.

FIG. 4A illustrates the results of the time-accumulation intensity curves of Samples 1a to 8a prepared from DPPC, DSPC and DSPE-PEG-2000 lipid mixture.

FIG. 4B illustrates the results of the relative accumulative intensity of Samples 1a to 8a prepared from DPPC, DSPC and DSPE-PEG-2000 lipid mixture where relative accumulative intensity value of 1a is normalized as 100%.

FIG. 6A illustrates the results of the time-accumulation intensity curves of Samples 1b to 8b prepared from DPPG, DSPC and DSPE-PEG-2000 lipid mixture.

FIG. 6B illustrates the results of the relative accumulative intensity of Samples 1b to 8b prepared from DPPG, DSPC and DSPE-PEG-2000 lipid mixture where relative accumulative intensity value of 1b is normalized as 100%.

FIGS. 7A-B show the concentrations of the formed microbubbles from Samples 1a, 3a, 6a, 3c, 6c (7A) and 1a, 3b, 6b, 3d, 6d (7B).

FIGS. 8A-B show the change of image intensity of microbubbles against time in each sample of 3a, 6a, 3c, 6c (8A), and 3b, 6b, 3d, 6d (8B).

FIGS. 8C-D illustrate the results of the time-accumulation intensity curve of Samples 3a, 6a, 3c, 6c (8C), and 3b, 6b, 3d, 6d (8D).

FIGS. 8E-F illustrate the results of the relative accumulative intensity of Samples 1a, 3a, 6a, 3c, 6c (8E) and 1a, 3b, 6b, 3d, 6d (8F) where relative accumulative intensity value of 1a is normalized as 100%.

FIG. 9A shows the concentrations of the formed microbubbles from Samples 1a, 3a, 6a, 3e and 6e.

FIG. 9B shows the change of image intensity of microbubbles against time in each sample of 3a, 6a, 3e and 6e.

FIG. 9C illustrates the results of the time-accumulation intensity curve of Samples 3a, 6a, 3e and 6e.

FIG. 9D illustrates the results of the relative accumulative intensity of Samples 1a, 3a, 6a, 3e and 6e where relative accumulative intensity value of 1a is normalized as 100%.

FIG. 10A shows concentrations of the formed microbubbles from Samples 1a, 6a, 6e, PEG40S_2 and PEG40S_3.

FIG. 10B shows the change of image intensity of microbubbles against time of Samples 1a, 6a, 6e, PEG40S_2 and PEG40S_3.

FIG. 10C illustrates the results of the time-accumulation intensity curve of Samples 6a, 6e, PEG40S_2 and PEG40S_3.

FIG. 10D illustrates the results of the relative accumulative intensity of Samples 1a, 6a, 6e PEG40S_2 and PEG40S_3 where relative accumulative intensity value of 1a is normalized as 100%.

FIG. 11A shows the concentrations of the formed microbubbles from Samples 1a, 3a, 5a, 3f and 5f.

FIG. 11B shows the change of image intensity of microbubbles against time in each sample of 3a, 5a, 3f and 5f.

FIG. 11C illustrates the results of the time-accumulation intensity curve of Samples 3a, 5a, 3f and 5f.

FIG. 11D illustrates the results of the relative accumulative intensity of Samples 1a, 3a, 5a, 3f and 5f where relative accumulative intensity value of 1a is normalized as 100%.

DETAILED DESCRIPTION OF THE INVENTION

Figure 3:
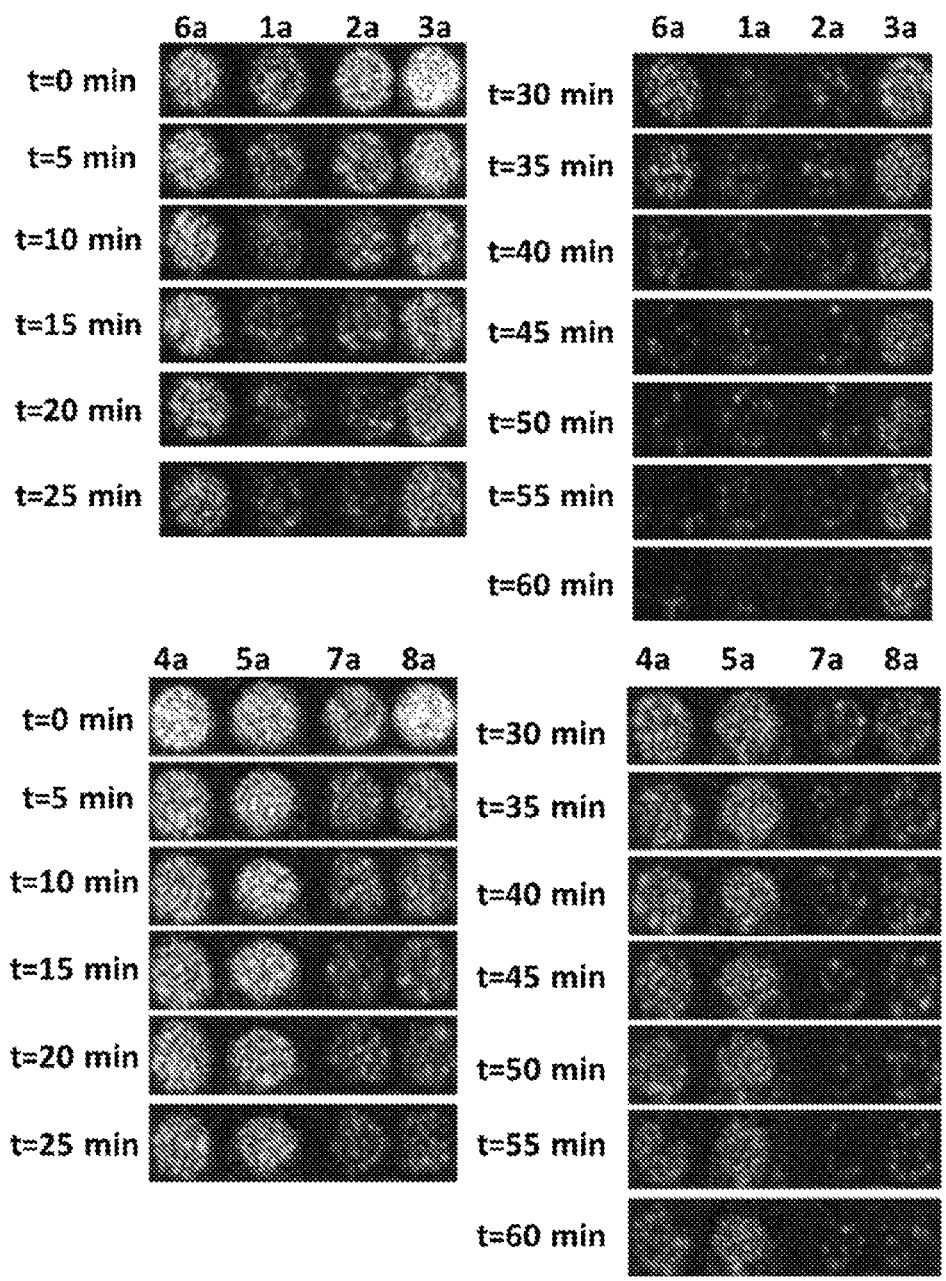
FIG. 3 shows the change of image intensity of microbubbles against time in each sample of 1a to 8a prepared from DPPC, DSPC and DSPE-PEG-2000 lipid mixture.

The Applicant has now unexpectedly found the specific compositions via a preferred method to produce invention microbubbles having excellent thermal stability and long in vivo stability that increase the longevity of effective time as ultrasound contrast agents.

It is known in the art that the imaging applications require relatively few microbubbles, for example, on the order of $10^6$-$10^8$ microbubbles per injection. Currently, the available micro-bubbles are relatively big in diameter and unstable in blood circulation, thus are hard to reach a sufficient accumulation in target tissue in a limited time.

The present invention, unexpectedly discovers a suspension of gas-filled microbubbles in a physiologically acceptable liquid carrier, with high concentration and excellent stability profile.

In particular, the present invention provides a suspension of gas-filled microbubbles in a physiologically acceptable liquid carrier comprising (a) a lipid mixture comprising a first lipid having transition temperature of about 41° C. such as DPPC or DPPG, a second lipid having transition temperature of about 55° C. such as DSPC or DSPG, and a PEGylated DSPE such as DSPE-PEG2000, DSPE-PEG3000, or DSPE-PEG5000, and (b) a biocompatible gas, wherein the ratio of said first lipid is in a range of about 40% to about 63% by weight in the lipid mixture. In certain embodiments, said first lipid is DPPC or DPPG. In certain embodiments, the ratio of said first lipid is in a range of 50% to 63% by weight, 40% to 60% by weight, 50% to 60% by weight, or 40% to 50% by weight. In certain embodiments, said first lipid is DPPC. In certain embodiments, said first lipid is DPPG. In certain embodiments, said second lipid is DSPC or DSPG. In certain embodiments, said second lipid is DSPC. In certain embodiments, said second lipid is DSPG. In certain embodiments, said PEGylated DSPE is DSPE-PEG2000, DSPE-PEG3000, or DSPE-PEG5000. In certain embodiments, said PEGylated DSPE is DSPE-PEG2000. In certain embodiments, the ratio of the PEGylated DSPE is about 10% to about 15% by weight. In certain embodiments, the ratio of the PEGylated DSPE is about 12.5% by weight. In certain embodiments, the suspension is in a seal vial. In certain embodiments provide the methods to prepare said suspension, or said seal vial. In certain embodiments, said suspension or seal vial further comprises 1% to 20% of glycerol. In certain embodiments, said suspension or seal vial further comprises 5% glycerol. In certain embodiments, said gas is selected from the group consisting of perfluorocarbons, $SF_6$, Ar and $N_2$. In certain embodiments, said perfluorocarbons gas is $C_3F_8$, $C_4F_{10}$, or $C_5F_{12}$.

In some embodiments provide a suspension of gas-filled microbubbles comprising (a) a lipid mixture comprising a first phospholipid having transition temperature of about 41° C. (such as DPPC or DPPG), a second phospholipid DSPC or DSPG, and a PEGylated DSPE such as DSPE-PEG2000, DSPE-PEG3000, or DSPE-PEG5000, and (b) a biocompatible gas, wherein the ratio of said first lipid is in a range of 40% to 63% by weight in the lipid mixture. In certain embodiments, the suspension is in a seal vial. In certain embodiments provide the methods to prepare said suspension, or said seal vial.

In some embodiments provide a suspension of gas-filled microbubbles comprising (a) a lipid mixture comprising a first lipid DPPC or DPPG, a second lipid having transition temperature of about 55° C. (such as DSPC or DSPG), and a PEGylated DSPE such as DSPE-PEG2000, DSPE-PEG3000, or DSPE-PEG5000, and (b) a biocompatible gas, wherein the ratio of said first lipid is in a range of 40% to 63% by weight in the lipid mixture. In certain embodiments, the suspension is in a seal vial. In certain embodiments provide the methods to prepare said suspension, or said seal vial.

In some embodiments provide a suspension of gas-filled microbubbles comprising (a) a lipid mixture comprising a first phospholipid DPPC or DPPG, a second phospholipid DSPC or DSPG, and a PEGylated-DSPE DSPE-PEG2000, DSPE-PEG3000, or DSPE-PEG5000, and (b) a biocompatible gas, wherein the ratio of said first phospholipid is in a range of 40% to 63% by weight in the lipid mixture. In certain embodiments, the suspension is in a seal vial. In certain embodiments provide the methods to prepare said suspension, or said seal vial.

In some embodiments provide a suspension of gas-filled microbubbles comprising (a) a lipid mixture comprising a first phospholipid having transition temperature of about 41° C. (such as DPPC or DPPG), a second phospholipid DSPC or DSPG, and DSPE-PEG2000, (where DSPE-2000 can be substituted with DSPE-PEG3000, or DSPE-PEG5000), and (b) a biocompatible gas, wherein the ratio of said first lipid is in a range of 40% to 63% by weight in the lipid mixture. In certain embodiments, the suspension is in a seal vial. In certain embodiments provide the methods to prepare said suspension, or said seal vial.

In some embodiments provide a suspension of gas-filled microbubbles comprising (a) a lipid mixture comprising either DPPC or DPPG, either DSPC or DPPG, and a PEGylated DSPE selected from DSPE-PEG2000, DSPE-PEG3000 and DSPE-PEG5000, and (b) a biocompatible gas, wherein the ratio of DPPC or DPPG is in a range of 40% to 63% by weight in the lipid mixture. In certain embodiments, the suspension is in a seal vial. In certain embodiments provide the methods to prepare said suspension, or said seal vial.

In some embodiments, examples of suitable first lipid having Tm of 41° C. are 1,2-dipalmitoyl-sn-glycero-3-phosphocholine (DPPC), 1,2-dipalmitoyl-sn-glycero-3-phospho-(1'-rac-glycerol) (DPPG), or the like, especially in a range of about 40% to about 63% by weight in the lipid mixture disclosed herein. In some embodiments, the ratio is in a range of 50% to 63% by weight, 40% to 60% by weight, 50% to 60% by weight, or 40% to 50% by weight in the lipid mixture disclosed herein.

In accordance with the unexpectedly finding of this invention, the ratio of DPPC is in a range of 40% to 63% by weight in the lipid mixture disclosed herein to provide a high concentration of microbubbles with superb stability profile. In certain embodiments, the ratio of DPPC is in a range of 50% to 60% by weight.

Similarly, the replacement of DPPC with the charged lipid DPPG also provides a high concentration of microbubbles with superb stability profile. In some embodiments, the ratio of DPPG is in a range of 40% to 63% by weight in the lipid mixture disclosed herein. In certain embodiments, the ratio of DPPG is in a range of 40% to 60%, or 40% to 50%, or 50% to 60% by weight.

In accordance with the practice of this invention, either 1,2-Distearoyl-sn-glycero-3-phosphocholine (DSPC), IUPAC name, [(2R)-2,3-Di(octadecanoyloxy)propyl] 2-(trimethylazaniumyl)ethyl phosphate, or 1,2-Dioctadecanoyl-sn-glycero-3-phospho-(1'-rac-glycerol) (DSPG) is used in the preferred lipid mixture disclosed herein for a suspension of gas-filled microbubbles that provide the unexpected superior results. Both DSPC and DSPG have transition temperature (Tm) of 55° C., thus it is expected that other lipids with the like properties and Tm would provide the same or similar unexpected results.

It was unexpected found that, contrary to the previous findings (e.g., US Publication No. 2009/0263330), the high content ratio of a polymer-modified lipid (e.g., DSPE-PEG2000, 12.5% w/w in the lipid mixture disclosed herein) do not negatively affect the amount of obtained microbubbles. Surprisingly, 10% to 15% w/w (e.g., 12.5% w/w) of DSPE-PEG2000, together with the preferred compositions of a low Tm lipid (e.g., DPPC and DPPG) mixed with a high Tm lipid (DSPC or DSPG) provide unexpected stabilized microbubbles.

Polymer modification, specifically polyethylene glycol (PEG)-lipid conjugations have been known in the art. A PEGylated lipid disclosed herein refers to a polyethylene glycol (PEG)-lipid conjugated lipid, e.g., 1,2-distearoyl-sn-glycero-3-phosphoethanolamine-N-[methoxy(polyethylene glycol)-2000] (DSPE-PEG2000), 1,2-distearoyl-sn-glycero-3-phosphoethanolamine-N-[methoxy(polyethylene glycol)-3000] (DSPE-PEG3000), 1,2-distearoyl-sn-glycero-3-phosphoethanolamine-N-[methoxy(polyethylene glycol)-5000] (DSPE-PEG5000), or the like.

As DSPE-PEG3000 and DSPE-PEG5000 all act similarly on the functions of DSPE-PEG2000, a PEGylated DSPE, in some instances, the unexpected results described herein are extended to these two PEGylated lipids. Example 4 shows the similar unexpected results when DSPE-PEG5000 was used instead of DSPE-PEG2000. In some embodiments, the ratio of the PEGylated DSPE such as DSPE-PEG2000, DSPE-PEG3000, or DSPE-PEG5000 in the lipid mixture is about 10% to about 15% by weight. In certain embodiments, the ratio of the PEGylated DSPE such as DSPE-PEG2000, DSPE-PEG3000, or DSPE-PEG5000 is about 12.5% by weight.

Gases disclosed herein suitable for use in microbubbles include for example, air, $O_2$, $N_2$, $H_2$, $CO_2$, $N_2O$, $SF_6$, noble gases, hydrocarbon gases, perfluorocarbon, other fluorinated gases and combinations thereof.

In certain embodiments, the gas used in the suspension of seal vial is selected from the group consisting of perfluorocarbon gas such as $C_3F_8$, $C_4F_{10}$, $C_5F_{12}$ or $SF_6$, or Ar, or $N_2$.

In some embodiments, the seal vial or the suspension disclosed herein further comprises 1% to 20% of glycerol. In certain embodiments, the seal vial or the suspension further comprises 5% of glycerol. The additional glycerol is used in accordance with the methods known in the field for microbubble preparations.

Non limited examples of suitable liquid carriers are water, typically sterile, pyrogen free water (to prevent as much as possible contamination in the intermediate lyophilized product), aqueous solutions such as saline (which may advantageously be balanced so that the final product for injection is not hypotonic), or aqueous solutions of one or more tonicity adjusting substances such as salts or sugars, sugar alcohols, glycols or other non-ionic polyol materials (e.g. glucose, sucrose, sorbitol, mannitol, glycerol, polyethylene glycols, propylene glycols and the like).

In some embodiments, the further comprising glycerol may be replaced with, for example, polyethylene glycol, peptide, albumin, amino acid, sugar alcohols, butane-1,3-diol, propane-1,2,3-triol, propane-1,2-diol, propane-1,3-diol, propan-1-ol, ethane-1,2-diol, ethanol, methanol and dimethyl sulfoxide, or a combination thereof.

Other excipients if used may comprise, for example, lactose, starch (e.g., corn starch), denatured corn starch, mannitol, lactose, sorbitol, wood cellulose, microcrystalline cellulose, combination thereof, or the like.

The binders if used may comprise, for example, hydroxypropyl cellulose, hydroxypropylmethyl cellulose, polyvinylpyrrolidone, polyvinyl alcohol, and partial saponificates of these, which can be used either singly or as combined.

The disintegrators if used may comprise, for example, low substituted hydroxypropyl cellulose, carmellose, sodium carboxy starch, calcium carmellose, sodium starch glycolate, kollidon CL, corn starch, partially-alphatized starch, Croscarmellose Sodium, Hydroxypropyl Cellulose, crospovidone (such as Crospovidone XL-10), combinations thereof, or the like.

The lubricants if used may comprise, for example, magnesium stearate, stearic acid, palmitic acid, calcium stearate, talc, combination thereof, or the like.

The term "acceptable" with respect to a formulation, composition or ingredient, as used herein, means having no persistent detrimental effect on the general health of the subject being treated.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

In certain embodiments, invention aqueous suspensions may include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

All of the various embodiments or options described herein can be combined in any and all variations. The following Examples serve only to illustrate the invention and are not to be construed in any way to limit the invention.

EXAMPLES

Example 1. Preparation of Microbubbles by Invention Formulations of DSPC Based Lipid Mixtures Design: To lower the overall Tm of the lipid mixture used in a suspension of gas-filled microbubbles, a lipid of lower Tm of about 41° C. (e.g., DPPC or DPPG, or the like) was used together with a lipid with higher Tm of about 55° C. (e.g., DSPC or DSPG, or the like).

Step 1: Preparation of the lipid mixture before gas filling: Dissolve the lipid mixtures of a first lipid (e.g., DPPC or DPPG), a second lipid (e.g., DSPC or DSPG) and a PEGylated lipid (e.g., DSPE-PEG2000) in accordance with the compositions of sample numbers shown in Tables 1 and 2 in a suitable organic solvent such as chloroform, methanol in each vial. The homogeneous lipid mixture film was formed after the removal of the organic solvent. Add 1 to 20% glycerol containing saline such as PBS (e.g., 5% glycerol PBS) to the resulted lipid mixture. Heat the aqueous lipid mixture, if needed, to generate a homogenous liposome solution. Dispense 0.8 mL of liposome solutions in a 2 mL glass vial. The concentration of the lipid mixtures in each vial was fixed at 4 mg/mL.

Step 2: Gas filling: Seal the vials prepared in Step 1 in a close chamber which contains perfluorocarbons gas, such as $C_3F_8$, $C_4F_{10}$, $C_5F_{12}$, or $SF_6$ or Ar or $N_2$. Alternatively, the vials can be purged with the desired gas before sealing. The gas filled vials were then stored in room temperature or under refrigeration waiting for the followed point-of-use formation of the bubbles.

Step 3: Right before each use or test, place the vials into an agitator to shake the liposome solution at room temperature (20-30° C.) until microbubble solution formed.

TABLE 1

Compositions of sample lipid mixtures comprising DPPC, DSPC and DSPE-PEG2000.

| Sample No. | Weight Ratio of DPPC (%) | Mole Ratio of DPPC (%) | DPPC (mg) | DSPC (mg) | *DSPE-PEG2000 (mg) | Calculated Effective Tm (° C.) |
|---|---|---|---|---|---|---|
| 1a | 0 | 0 | 0 | 14 | 2 | 55 |
| 2a | 20 | 23.2 | 3.2 | 10.8 | 2 | 52.2 |
| 3a | 40 | 45.8 | 6.4 | 7.6 | 2 | 49.4 |
| 4a | 50 | 55.8 | 8 | 6 | 2 | 48 |
| 5a | 60 | 67.6 | 9.6 | 4.4 | 2 | 46.6 |
| 6a | 62.5 | 70.20 | 10 | 4 | 2 | 45 |
| 7a | 80 | 88.63 | 12.8 | 1.2 | 2 | 43.8 |
| 8a | 87.5 | 96.40 | 14 | 0 | 2 | 42.75 |

Note:
*The weight ratio (%) of DSPE-PEG2000 is fixed at a ratio of about 12.5%, i.e. a mole ratio from 3.6 to 3.9% for each formulation.

TABLE 2

Compositions of sample lipid mixtures comprising DPPG, DSPC and DSPE-PEG2000.

| Sample No. | Weight Ratio of DPPG (%) | Mole Ratio of DPPG (%) | DPPG (mg) | DSPC (mg) | *DSPE-PEG2000 (mg) | Calculated Effective Tm (° C.) |
|---|---|---|---|---|---|---|
| 1b | 0 | 0 | 0 | 14 | 2 | 55 |
| 2b | 20 | 23.22 | 3.2 | 10.8 | 2 | 52.2 |
| 3b | 40 | 45.77 | 6.4 | 7.6 | 2 | 49.5 |
| 4b | 50 | 55.76 | 8 | 6 | 2 | 48 |
| 5b | 60 | 67.58 | 9.6 | 4.4 | 2 | 46.6 |
| 6b | 62.5 | 70.20 | 10 | 4 | 2 | 45 |
| 7b | 80 | 88.63 | 12.8 | 1.2 | 2 | 43.8 |
| 8b | 87.5 | 96.40 | 14 | 0 | 2 | 42.75 |

Note:
*The weight ratio (%) of DSPE-PEG2000 is fixed at a ratio of 12.5%, i.e. a mole ratio from 3.6 to 3.9% for each formulation.

Example 2. Measurements of the Formed Microbubbles From Exemplary Formulations

The formed microbubbles in each vial were evaluated by Multisizer to determine microbubble's mean size and concentration. The results are shown in Tables 3 and 4 and FIGS. 1 and 2.

TABLE 3

Microbubbles mean size the concentration prepared from DPPC, DSPC and DSPE-PEG2000 lipid mixture.

| Sample No. | Concentration (bubble/mL) | mean size (μm) |
|---|---|---|
| 1a | $(9.82 \pm 0.66) \times 10^9$ | $1.03 \pm 0.10$ |
| 2a | $(19.65 \pm 0.92) \times 10^9$ | $1.25 \pm 0.08$ |
| 3a | $(25.46 \pm 0.35) \times 10^9$ | $1.26 \pm 0.04$ |
| 4a | $(29.23 \pm 0.36) \times 10^9$ | $1.29 \pm 0.06$ |
| 5a | $(23.91 \pm 2.57) \times 10^9$ | $1.51 \pm 0.06$ |
| 6a | $(24.95 \pm 1.53) \times 10^9$ | $1.34 \pm 0.07$ |
| 7a | $(16.34 \pm 1.34) \times 10^9$ | $1.23 \pm 0.04$ |
| 8a | $(19.45 \pm 1.90) \times 10^9$ | $1.16 \pm 0.05$ |

TABLE 4

Microbubbles mean size the concentration prepared from DPPG, DSPC and DSPE-PEG2000 lipid mixture.

| Sample No. | Concentration (bubble/mL) | mean size (μm) |
|---|---|---|
| 1b | $(9.82 \pm 0.66) \times 10^9$ | $1.03 \pm 0.10$ |
| 2b | $(18.45 \pm 1.56) \times 10^9$ | $1.30 \pm 0.06$ |
| 3b | $(22.60 \pm 1.40) \times 10^9$ | $1.45 \pm 0.03$ |
| 4b | $(29.02 \pm 0.80) \times 10^9$ | $1.47 \pm 0.01$ |
| 5b | $(20.19 \pm 0.63) \times 10^9$ | $1.56 \pm 0.03$ |
| 6b | $(25.79 \pm 2.13) \times 10^9$ | $1.09 \pm 0.02$ |
| 7b | $(12.28 \pm 2.60) \times 10^9$ | $1.68 \pm 0.09$ |
| 8b | $(8.62 \pm 1.08) \times 10^9$ | $1.66 \pm 0.08$ |

FIGS. 1A-B show concentrations and mean size of the formed microbubbles by sample numbers 1a-8a. FIGS. 2A-B show concentrations and mean size of the formed microbubbles by sample numbers 1b-8b.

As clearly shown, samples of 40% to 62.5% w/w of DPPC (Tm=41° C., a charge neutral lipid) used with DSPC (Tm=55° C.) and DSPE-PEG-2000 provided better results, based on the concentrations and mean size of the formed microbubbles.

Similarly, samples of 40% to 62.5% w/w of DPPG (Tm=41° C., a charged lipid) used with DSPC (Tm=55° C.) and DSPE-PEG-2000 provided better results, based on the concentrations and mean size of the formed microbubbles.

The data shows that the exemplary samples of 40% to 62.5% w/w ratio of the first lipid (with or without charge) that has a lower transition temperature (Tm=41° C.) with a second lipid DSPC (higher Tm of 55° C.), and 12.5% w/w of DSPE-PEG-2000 provide high concentrations with small mean size microbubbles.

Example 3. Stability Evaluation of the Formed Microbubbles From Exemplary Formulations The formed microbubbles in each vial were test for their stability under 37° C.—human application condition. The microbubbles were diluted 8000 folds with saline solution and placed in phantom at 37° C. The temperature was maintained throughout the whole test. The image of the resulting microbubble solution was then taken every minute under ultrasound contrast imaging conditions to record the intensity of each sample using the clinical ultrasound model of Philips CX-50. Matlab software was used to handle the acquired images, where the contrast intensity was calculated from the color level of each pixel and further present using arb. unit (a.u.).

FIG. 3 shows the change of image intensity of microbubbles against time in each sample 1a to 8a. The contrast intensity of ultrasound images by each sample (1a-8a) was calculated and accumulated over time to compare the echo performance between each sample.

The present invention aimed to provide a robust bubble contrast agent for ultrasound imaging. Two key aspects should be considered together, i.e. contrast enhancement under ultrasound imaging and persistence of bubbles (effective imaging half-life of bubbles). In clinical practices, good echo enhancement with a long persistence is highly sought. For example, for the diagnosis of local liver lesion, an effective imaging half-life longer than 10 minutes was recommended. Thus, accumulating method was used in the present invention to describe the overall echo performance of each formulation rather than using initial contrast intensities.

The contrast intensity of each ultrasound images in each sample was firstly quantified and was then accumulated over time. The contrast intensity from each minute was accumulated. The time interval was set at 50 minutes. Bubble with good contrast enhancement and persistence would suggest a larger accumulative intensity on the last time point, i.e. 50 minutes.

Based on the value of the contrast intensity accumulated for 50 minutes from the beginning of the study (see Table 5 below), the time-accumulation intensity curves of Samples 1a to 8a are provided in FIG. 4A.

TABLE 5

Accumulative intensity of 1a to8a.

| | |
|---|---|
| 1a | 15915 ± 4018 |
| 2a | 20227 ± 8789 |
| 3a | 35182 ± 2854 |
| 4a | 35018 ± 6654 |
| 5a | 36755 ± 5021 |
| 6a | 32997 ± 6459 |
| 7a | 15739 ± 6722 |
| 8a | 16443 ± 7774 |

By normalizing the accumulative intensity value of 1a as 100%, the comparison results of relative accumulative intensity of sample 1a to 8a are shown in FIG. 4B.

The results indicate that Samples 3a, 4a, 5a, and 6a, ranging from 40% to 62.5% of DPPC by weight in the lipid mixture, have a significant difference and improvement over Samples 1a, 2a, 7a, and 8a.

The stability test results show that 40% to 62.5% w/w of DPPC (Tm=41° C., neutral lipid) used with DSPC (Tm=55° C.) and DSPE-PEG-2000 provided stable microbubbles useful in imaging purposes. Based on this finding, the transition temperature (Tm) of the microbubbles prepared from the lipid mixtures of DPPC, DSPC, and DSPE-PEG-2000 ranges from 45 to 49.5° C. The results also indicate that 40% to 60% w/w of DPPC used with DSPC/DSPE-PEG-2000 provides even more stable microbubbles useful for imaging purpose. The transition temperature (Tm) of the preferred stabilized microbubbles prepared from the lipid mixtures of DPPC, DSPC, and DSPE-PEG-2000 ranges from 46.6 to 49.5° C.

Figure 5:
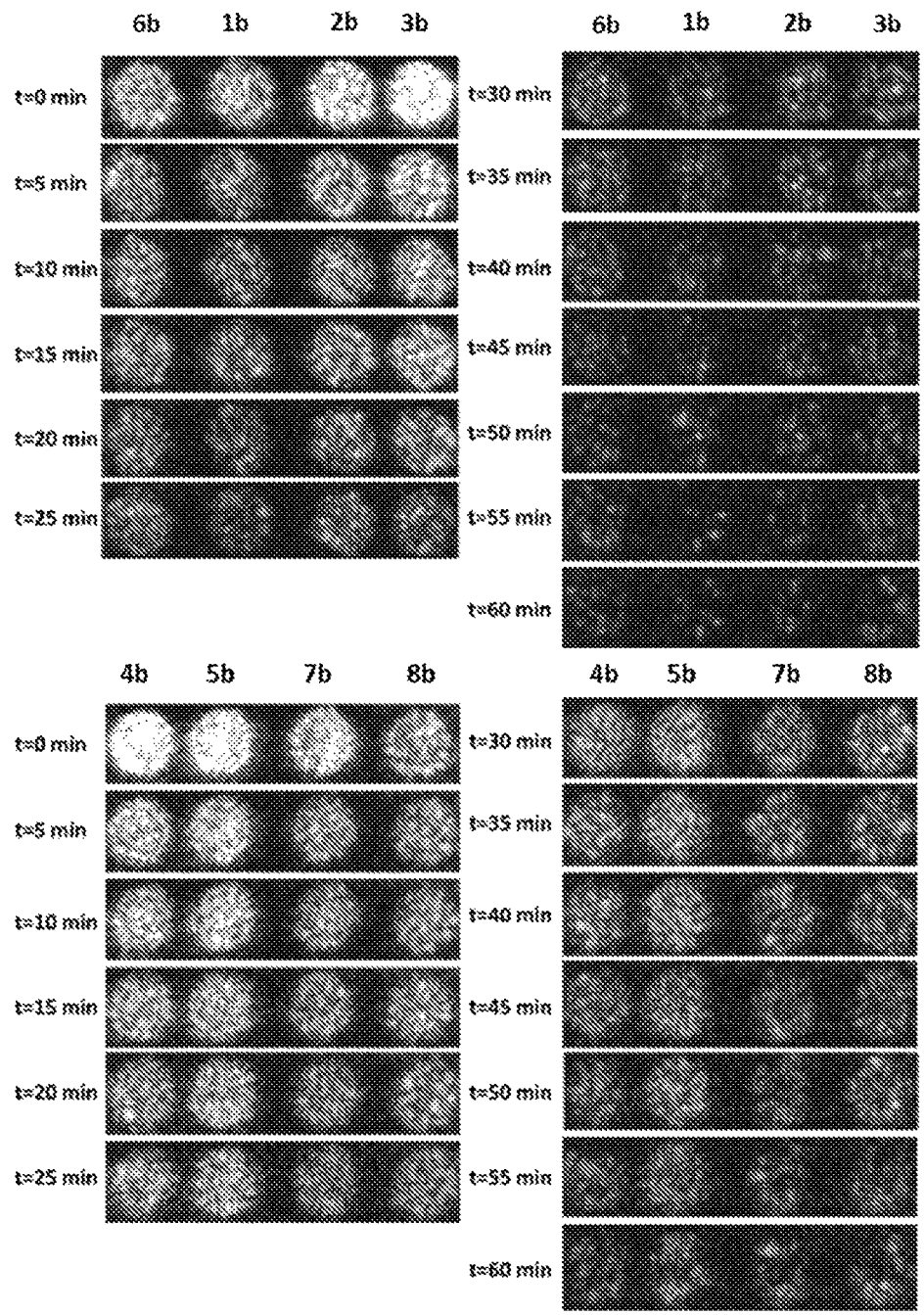
FIG. 5 shows the change of image intensity of microbubbles against time in each sample of 1b to 8b prepared from DPPG, DSPC and DSPE-PEG-2000 lipid mixture.

FIG. 5 shows the change of image intensity of microbubbles against time in each sample 1b to 8b. The contrast intensity of ultrasound images by each sample (1b-8b) based on the formulations prepared from DPPG, DSPC and DSPE-PEG-2000 lipid mixture was calculated and accumulated over time to compare the echo performance between each sample.

Based on the value of the contrast intensity accumulated for 50 minutes from the beginning of the study (see Table 6 below), the time-accumulation intensity curves of Sample 1b to 8b are provided in FIG. 6A.

TABLE 6

Accumulative intensity of Samples 1b to 8b.

| | |
|---|---|
| 1b | 15915 ± 4018 |
| 2b | 19476 ± 5670 |
| 3b | 39130 ± 2536 |
| 4b | 37525 ± 5811 |
| 5b | 40466 ± 6620 |
| 6b | 46710 ± 3192 |
| 7b | 23848 ± 11483 |
| 8b | 26713 ± 8342 |

By normalizing accumulative intensity value using 1b as 100%, FIG. 6B provides the results of relative accumulative intensity of each sample of 1b to 8b.

The results indicate that Samples 3b, 4b, 5b, and 6b, ranging from 40% to 62.5% of DPPG by weight, have a significant difference and improvement over Samples 1b, 2b, 7b, and 8b.

Similarly, the stability test results show that 40% to 62.5% w/w of DPPG (Tm=41° C., charged lipid) used with DSPC (Tm=55° C.) and DSPE-PEG-2000 provided stable microbubbles useful in imaging purposes. Based on this finding, the transition temperature (Tm) of the microbubbles prepared from the lipid mixtures of DPPG, DSPC, and DSPE-PEG2000 ranges from 45 to 49.5° C. In some embodiments, 62.5% w/w of DPPG used with DSPG and DSPE-PEG2000 provides even more stable microbubbles useful for imaging purpose.

In summary, the data shows that 40% to 62.5% w/w ratio of the low Tm lipid with or without charge (e.g., DPPC, and DPPG, Tm=41° C.) together with a higher Tm lipid such as DSPC (Tm=55° C.), and about 12.5% w/w of DSPE-PEG2000 provide microbubbles with very good stability profile under human application condition (e.g., at 37° C.).

Example 4. Stability Evaluation of the Formed Microbubbles by the PEGylated DSPE Containing Formulations The formed microbubbles in each vial were test for their stability under 37° C.—human application condition as described in Example 3. Here, the study is aimed to determine if a similar PEGylated DSPE such as DSPE-PEG3000 or DSPE-PEG5000 used in the lipid mixture can provide the similar unexpected results. An exemplary DSPE-PEG5000 was used in the study.

The lipid mixtures were prepared in accordance with the compositions shown in Tables 7 and 8.

TABLE 7

Compositions of sample lipid mixtures comprising a first lipid DPPC, a second lipid DSPC and DSPE-PEG2000 or DSPEPEG5000.

| Sample No. | DPPC (mg) | DSPC (mg) | DSPE-PEG2k (mg) | DSPE-PEG5k (mg) | Calculated Effective Tm (° C.) |
|---|---|---|---|---|---|
| 3a | 6.4 | 7.6 | 2 | — | 49.5 |
| 6a | 10 | 4 | 2 | — | 45 |
| 3c | 6.4 | 7.6 | — | 2 | 49.5 |
| 6c | 10 | 4 | — | 2 | 45 |

TABLE 8

Compositions of sample lipid mixtures comprising a first lipid DPPG, a second lipid DSPC and DSPE-PEG-2000 or DSPE-PEG5000.

| Sample No. | DPPG (mg) | DSPC (mg) | DSPE-PEG2k (mg) | DSPE-PEG5k (mg) | Calculated Effective Tm (° C.) |
|---|---|---|---|---|---|
| 3b | 6.4 | 7.6 | 2 | — | 49.5 |
| 6b | 10 | 4 | 2 | — | 45 |
| 3d | 6.4 | 7.6 | — | 2 | 49.5 |
| 6d | 10 | 4 | — | 2 | 45 |

The formed microbubbles in each vial were evaluated by Multisizer to determine microbubble's mean size and concentration. The results are shown in Tables 9 and 10.

TABLE 9

Microbubbles mean size the concentration of Samples 3a, 6a, 3c and 6c.

| Sample No. | Concentration (bubble/mL) | Mean size (μm) |
|---|---|---|
| 3a | $(25.46 \pm 0.35) \times 10^9$ | $1.26 \pm 0.04$ |
| 6a | $(24.95 \pm 1.53) \times 10^9$ | $1.34 \pm 0.07$ |
| 3c | $(28.41 \pm 1.75) \times 10^9$ | $1.25 \pm 0.02$ |
| 6c | $(28.64 \pm 4.18) \times 10^9$ | $1.42 \pm 0.10$ |

TABLE 10

Microbubbles mean size the concentration of Samples 3b, 6b, 3d and 6d.

| Sample No. | Concentration (bubble/mL) | Mean size (μm) |
|---|---|---|
| 3b | $(22.60 \pm 1.40) \times 10^9$ | $1.45 \pm 0.03$ |
| 6b | $(25.79 \pm 2.13) \times 10^9$ | $1.09 \pm 0.02$ |
| 3d | $(23.49 \pm 1.91) \times 10^9$ | $1.35 \pm 0.05$ |
| 6d | $(25.84 \pm 3.91) \times 10^9$ | $1.43 \pm 0.06$ |

As shown in Table 9, the concentrations and mean size of the formed microbubbles from sample 3a and 3c are very similar and comparable; the concentrations and mean size of the formed microbubbles from sample 6a and 6c are very similar and comparable as well. Especially as shown in FIG. 7A, where the microbubbles concentrations of 1a, 3a, 6a, 3c, and 6c are compared, the group of 3a, 6a, 3c and 6c appears to have high concentration in comparison with one of 1a.

As shown in Table 10, the concentrations and mean size of the formed microbubbles from sample 3b and 3d are very similar and comparable; the concentrations and mean size of the formed microbubbles from sample 6b and 6d are very similar and comparable as well. Especially as shown in FIG. 7B, where the microbubbles concentrations of 1a, 3b, 6b, 3d, and 6d are compared, the group of 3b, 6b, 3d and 6d appears to have high concentration in comparison with one of 1a.

Next, the image of the resulting microbubble solution from 1a, 3a, 6a, 3c and 6c respectively, was then taken every minute under ultrasound contrast imaging conditions to record the intensity of each sample. The results are shown in FIG. 8A. The similar results for 1a, 3b, 6b, 3d and 6d respectively are shown in FIG. 8B.

The contrast intensity of ultrasound images by sample 3a, 6a, 3b, 6b, 3c, 6c, 3d, and 6d respectively was calculated and accumulated over time to compare the echo performance of each sample. Based on the value of the contrast intensity accumulated for 50 minutes from the beginning of the study (see Tables 11 and 12 below), the time-accumulation intensity curve of each sample is provided in FIGS. 8C and 8D.

TABLE 11

Accumulative intensity of sample 3a, 6a, 3c and 6c where DSPE-PEG2000 or DSPE-PEG5000 was used in the lipid mixture.

| 3a | 35182 ± 2854 |
| 6a | 32997 ± 6459 |
| 3c | 28084 ± 5110 |
| 6c | 36767 ± 3892 |

TABLE 12

Accumulative intensity of sample 3b, 6b, 3d and 6d where DSPE-PEG2000 or DSPE-PEG5000 was used in the lipid mixture.

| 3b | 39130 ± 2536 |
| 6b | 46710 ± 3192 |
| 3d | 47916 ± 1907 |
| 6d | 48128 ± 3874 |

By normalizing accumulative intensity value of 1a as 100%, the results of relative accumulative intensity of sample 1a, 3a, 6a, 3c and 6c are shown in FIG. 8E where the group of 3a, 3c, 6a, and 6c provide the superior relative accumulative intensity compared with one of 1a. The results showed that Samples 3a and 6a (DPPC with DSPE-PEG2000) have no significant difference with Samples 3c and 6c (DPPC with DSPE-PEG5000) in term of providing a similar high stability profile.

By normalizing the accumulative intensity value of 1a as 100%, the results of relative accumulative intensity of Samples 1a, 3b, 6a, 3d and 6d are shown in FIG. 8F where Samples 3b, 6a, 3d and 6d provide the superior relative accumulative intensity compared with one of 1a. The results showed that Samples 3b and 6b (DPPG with DSPE-PEG2000) have no significant difference with Samples 3d and 6d (DPPG with DSPE-PEG5000) in term of providing a similar high stability profile.

Thus, it is clear that the unexpected benefit from the use of DSPE-PEG2000 can be extended to the similar components DSPE-PEG3000 and DSPE-5000.

Example 5. Microbubbles Stability Comparison Between Formulations Containing DSPC or DSPG The formed microbubbles in each vial were test for their stability under 37° C.—human application condition as described in Example 3. Here, a second phospholipid DSPG with the same Tm was used in the lipid mixture to prepare microbubbles under the same similar process of making conditions. The test is to evaluate if the unexpected results shown in Examples 1-4 can be extended to a different second phospholipid with same or similar Tm.

The lipid mixtures were prepared in accordance with the compositions shown in Table 13 where the first lipid DPPC with DSPE-PEG2000 were used.

TABLE 13

Compositions of sample lipid mixtures comprising a first lipid DPPC, a second lipid DSPC or DSPG and DSPE-PEG-2000.

| Sample No. | DPPC (mg) | DSPC (mg) | DSPG (mg) | DSPE-PEG2k (mg) | Calculated Effective Tm (° C.) |
|---|---|---|---|---|---|
| 3a | 6.4 | 7.6 | — | 2 | 49.5 |
| 6a | 10 | 4 | — | 2 | 45 |
| 3e | 6.4 | — | 7.6 | 2 | 49.5 |
| 6e | 10 | — | 4 | 2 | 45 |

The formed microbubbles in each vial were evaluated by Multisizer to determine microbubble's mean size and concentration. The results are shown in Table 14.

TABLE 14

Microbubbles mean size the concentration of Sample 3a, 6a, 3e and 6e.

| Sample No. | Concentration (bubble/mL) | Mean size (μm) |
|---|---|---|
| 3a | $(25.46 \pm 0.35) \times 10^9$ | $1.26 \pm 0.04$ |
| 6a | $(24.95 \pm 1.53) \times 10^9$ | $1.34 \pm 0.07$ |
| 3e | $(24.62 \pm 3.96) \times 10^9$ | $1.26 \pm 0.11$ |
| 6e | $(22.14 \pm 2.29) \times 10^9$ | $1.35 \pm 0.17$ |

As shown in Table 14, the concentrations and mean size of the formed microbubbles from sample 3a and 3e are very similar and comparable; the concentrations and mean size of the formed microbubbles from sample 6a and 6e are very similar and comparable as well. Especially as shown in FIG. 9A, where the microbubbles concentrations of Samples 1a, 3a, 6a, 3e, and 6e are compared, the group of Samples 3a, 6a, 3e and 6e appears to have high concentration in comparison with one of 1a.

Next, the image of the resulting microbubble solution from 3a, 6a, 3e and 6e respectively, was then taken every minute under ultrasound contrast imaging conditions to record the intensity of each sample. The results are shown in FIG. 9B.

The contrast intensity of ultrasound images by Samples 3a, 6a, 3e, and 6e respectively was calculated and accumulated over time to compare the echo performance of each sample. Based on the value of the contrast intensity accumulated for 50 minutes from the beginning of the study (see Tables 15), the time-accumulation intensity curve of each sample is provided in FIG. 9C.

TABLE 15

Accumulative intensity of Sample 3a, 6a, 3e and 6e where DSPC or DSPG was used in the lipid mixture

| 3a | 35182 ± 2854 |
| 6a | 32997 ± 6459 |
| 3e | 36464 ± 4702 |
| 6e | 34590 ± 3767 |

By normalizing the accumulative intensity value of 1a as 100%, the results of relative accumulative intensity of Sample 1a, 3a, 6a, 3e and 6e are shown in FIG. 9D where the group of 3a, 3e, 6a, and 6e provide the superior relative accumulative intensity compared with one of 1a. The results showed that the group of Samples 3a and 6a (with DSPC) have no significant difference with the group of Samples 3e and 6e (with DSPG).

Thus, it is clear that the unexpected benefit from the use of DSPC can be extended to the similar components DSPG.

Example 6. Stability Test of Invention Formulations in Comparison with the Known Formulation with a Different PEGylated Lipid The exemplary formulations (e.g., Samples 6a and 6e) were further subject to a stability test in comparison with the known formulations disclosed in US Publication No. 2014328767. The selected formulations and the exemplary invention formulation all have overall Tm of 45° C. of the lipid mixtures. The preparation method for each sample tested was the same under the condition as shown in Example 1. The composition of each sample is shown in Table 16.

TABLE 16

Compositions of sample lipid mixtures comprising a first lipid DPPC, a second lipid DSPC or DSPG and DSPE-PEG-2000 or PEG40s

| Sample | DPPC (mg) | DSPC (mg) | DSPG (mg) | *DSPE-PEG-2000 (mg) | PEG40S (mg) | Calculated Effective Tm (° C.) |
|---|---|---|---|---|---|---|
| 6a | 10 | 4 | — | 2 | — | 45 |
| 6e | 10 | — | 4 | 2 | — | 45 |
| PEG40S_2 | 10 | — | 4 | — | 2 | 45 |
| PEG40S_3 | 10 | — | 4 | — | 3 | 45 |

The formed microbubbles in each sample were evaluated by Multisizer to determine microbubble's mean size and concentration. The results are shown in Table 17. FIG. 10A shows concentrations of the formed microbubbles from sample 1a, 6a, 6e and PEG40S_2 and PEG40S_3.

TABLE 17

Stability study of exemplary microbubbles prepared by samples 6a, 6e, PEG40s_2 and PEG40s_3.

| Sample No. | Concentration (bubble/mL) | mean size (μm) |
|---|---|---|
| 6a | $(24.95 \pm 1.53) \times 10^9$ | $1.34 \pm 0.07$ |
| 6e | $(22.14 \pm 2.29) \times 10^9$ | $1.35 \pm 0.17$ |
| PEG40S_2 | $(12.53 \pm 0.93) \times 10^9$ | $1.29 \pm 0.07$ |
| PEG40S_3 | $(8.62 \pm 0.45) \times 10^9$ | $1.21 \pm 0.02$ |

As shown in Table 17, the concentrations of the formed microbubbles from sample 6a and 6e where DSPE-PEG-2000 was used provide much better unexpected high concentration in comparison with ones from sample PEG40s_2 and PEG40s_3.

It is clearly shown that Samples 6a and 6e have higher concentration than those of PEG40S_2 and PEG40S_3, while the means size of these three samples are in the similar range of 1.2 to 1.5 μm. Despite they all have the overall Tm of 45° C., the exemplary invention formulations (e.g., Samples 6a and 6e) provides 2 to 3 folds' higher concentration. It is unexpected to see the different PEGylated lipid (i.e., DSPE-PEG2000) with similar ratio play a very important role to create more microbubbles.

These three samples were also subject to the same stability evaluation as shown in Example 3. The image of the resulting microbubble solution from Samples 6a, 6e, PEG40S_2 and PEG40S_3 respectively, was then taken every minute under ultrasound contrast imaging conditions to record the intensity of each sample. The results are shown in FIG. 10B.

The contrast intensity of ultrasound images by Samples 6a, 6e, PEG40S_2 and PEG40S_3 respectively was calculated and accumulated over time to compare the echo performance of each sample. Based on the value of the contrast intensity accumulated for 50 minutes from the beginning of the study (see Table 18 below), the time-accumulation intensity curve of each sample is provided in FIG. 10C.

TABLE 18

Accumulative intensity of sample 6a, 6e, PEG40S_2 and PEG40S_3.

| | |
|---|---|
| 6a | 32997 ± 6459 |
| 6e | 34590 ± 3767 |
| PEG40S_2 | 18204 ± 6333 |
| PEG40S_3 | 21752 ± 11778 |

By normalizing 1a accumulative intensity value as 100%, the results of relative accumulative intensity of sample 1a, 6a, 6e, PEG40S_2 and PEG40S_3 are shown in FIG. 10D.

It is clearly shown that Samples 6a and 6e have a better stability profile against Sample PEG40S_2 and PEG40S_3. The particular invention formulations provide a unique and unexpected stability profile against the known formulations despite they all have the overall Tm of 45° C. This unexpected superb stability profile with high concentration and superb stability of invention microbubbles disclosed herein provide broad human applications.

Example 7. Direct Comparison Study of Low Tm First Lipids

To further investigate potential lipids suitable for forming microbubbles with high stability profile, a lipid with lower Tm value, i.e. 15:0 PC (1,2-dipentadecanoyl-sn-glycero-3-phosphocholine, Tm=35° C.), was used in the lipid mixture to prepare microbubbles in comparison with the samples with the first lipid having Tm of 41. 15:0 PC is a synthesized phospholipid which has a chemical structure similar to that of DPPC and DPPG (Tm=41° C.) with a shorter carbon chain of 15 carbons rather than 16 carbons of DPPC or DPPG.

The lipid mixtures were prepared in accordance with the compositions shown in Table 19 where the first lipid DPPC or 15:0 PC, the second lipid DSPC, and DSPE-PEG2000 were used.

TABLE 19

Compositions of Samples 3a, 5a, 3f, and 5f.

| Sample No. | Weight ratio of DPPC (%) | Weight ratio of 15:0 PC (%) | DPPC (mg) | 15:0 PC (mg) | DSPC (mg) | DSPE-PEG2k (mg) | Calculated Effective Tm (° C.) |
|---|---|---|---|---|---|---|---|
| 3a | 40 | — | 6.4 | — | 7.6 | 2 | 49.4 |
| 5a | 60 | — | 9.6 | — | 4.4 | 2 | 45 |
| 3f | — | 40 | — | 6.4 | 7.6 | 2 | 47 |
| 5f | — | 60 | — | 9.6 | 4.4 | 2 | 43 |

The formed microbubbles in each vial were evaluated by Multisizer to determine microbubble's mean size and concentration. The results are shown in Table 20.

TABLE 20

Microbubbles mean size the concentration of Samples 3a, 5a, 3f, and 5f.

| Sample No. | Concentration (bubble/mL) | Mean size (μm) |
|---|---|---|
| 3a | (25.46 ± 0.35) × 10$^9$ | 1.26 ± 0.04 |
| 5a | (23.91 ± 2.57) × 10$^9$ | 1.51 ± 0.06 |
| 3f | (1.33 ± 0.06) × 10$^9$ | 1.59 ± 0.02 |
| 5f | (0.50 ± 0.06) × 10$^9$ | 1.28 ± 0.08 |

As shown in Table 20, the concentrations of Samples 3f and 5f showed a significant difference with those of 3a and 3b. Especially as shown in FIG. 11A, where the microbubbles concentrations of 1a, 3a, 5a, 3f, and 5f are compared, the group of 3a, and 5a appears to have high concentration in comparison with ones of 3f and 5f, which is even lower that one of 1a. The low concentrations suggested that the samples with 15:0 PC, i.e. 3f and 5f, were not successfully activated under this condition. The result also suggested that the formulations of 3f and 5f are not suitable for generating bubbles with high stability profile. All formulations in this test were further put into ultrasound imaging examinations.

The images of the resulting microbubble solution from Samples 3a, 5a, 3f and 5f respectively, were then taken every minute under ultrasound contrast imaging conditions to record the intensity of each sample. The results are shown in FIG. 11B.

The contrast intensity of ultrasound images by Samples 3a, 5a, 3f and 5f respectively was calculated and accumulated over time to compare the echo performance of each sample. Based on the value of the contrast intensity accumulated for 50 minutes from the beginning of the study (see Tables 21), the time-accumulation intensity curve of each sample is provided in FIG. 10C.

TABLE 21

Accumulative intensity of Samples 3a, 5a, 3f and 5f.

| | |
|---|---|
| 3a | 35182 ± 2854 |
| 5a | 36755 ± 5021 |
| 3f | 14382 ± 3472 |
| 5f | 3163 ± 1260 |

By normalizing 1a accumulative intensity value as 100%, the results of relative accumulative intensity of sample 1a, 3a, 5a, 3f and 5f are shown in FIG. 11D. Samples 3f and 5f were directly compared with Samples 3a and 5a side by side. The results showed that the samples with a first lipid having transition temperature of about 41° C. have a 2.44 to 11.62 folds' improvement compared with the samples using 15:0 PC with Tm of 35° C. The results further confirm the unexpected benefit that a first lipid having transition temperature of about 41° C. (e.g., DPPC and DPPG) form stable lipid microbubbles with longevity. A first lipid with lower Tm although may lower the Tm of the lipid mixture, it does not provide a better result.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A suspension of gas-filled microbubbles in a physiologically acceptable liquid carrier, said microbubbles consisting of (a) a lipid mixture consisting of a first lipid wherein said first lipid is DPPC or DPPG, a second lipid wherein said second lipid is DSPC or DSPG, and a PEGylated DSPE wherein said PEGylated DSPE is DSPE-PEG2000, DSPE-PEG3000, or DSPE-PEG5000, and (b) a biocompatible gas, wherein said first lipid is in a range of 40% to 63% by weight in the lipid mixture, and wherein the PEGylated DSPE is 12.5% by weight.

2. The suspension of claim 1, wherein the second lipid is in a range of 25% to 47.5% by weight.

3. The suspension of claim 1, wherein said first lipid is in a range of 50% to 63% by weight.

4. The suspension of claim 1, wherein said first lipid is in a range of 40% to 60% by weight.

5. The suspension of claim 1, wherein said first lipid is DPPC.

6. The suspension of claim 1, wherein said first lipid is DPPG.

7. The suspension of claim 1, wherein said suspension further comprises 1% to 20% of glycerol.

8. The suspension of claim 1, wherein said suspension further comprises 5% of glycerol.

9. The suspension of claim 1, wherein said gas is selected from the group consisting of perfluorocarbons, $SF_6$, Ar and $N_2$.

10. The suspension of claim 9, wherein said perfluorocarbons gas is $C_3F_8$, $C_4F_{10}$, or $C_5F_{12}$.

11. A sealed vial comprising a suspension of gas-filled microbubbles of claim 1.

12. The sealed vial of claim 11, wherein said gas is selected from the group consisting of perfluorocarbons gas, $SF_6$, Ar and $N_2$.

* * * * *